United States Patent [19]

Ife et al.

[11] Patent Number: 4,806,550

[45] Date of Patent: Feb. 21, 1989

[54] 4-AMINO-3-CARBONYL SUBSTITUTED QUINOLINES AS INHIBITORS OF GASTRIC ACID SECRETION

[75] Inventors: Robert J. Ife, Stevenage; Thomas H. Brown, Tewin; Colin A. Leach, Stevenage, all of England

[73] Assignee: SmithKline & French Laboratories Limited, Welwyn Garden City, United Kingdom

[21] Appl. No.: 192,996

[22] Filed: May 12, 1988

Related U.S. Application Data

[63] Continuation of Ser. No. 92,749, Sep. 3, 1987.

[30] Foreign Application Priority Data

Sep. 5, 1986 [GB] United Kingdom ............... 8621425

[51] Int. Cl.[4] .............................................. A61K 31/47
[52] U.S. Cl. .................................... 514/313; 546/159; 546/160; 546/161; 546/162
[58] Field of Search ......................................... 514/313

[56] References Cited

U.S. PATENT DOCUMENTS 4,343,804  8/1982  Munson, Jr. et al. ............... 546/159

FOREIGN PATENT DOCUMENTS 184322  6/1986  European Pat. Off. .
191603  8/1986  European Pat. Off. .
193329  9/1986  European Pat. Off. .

OTHER PUBLICATIONS

Godard et al., *J. Het Chem;* 17, 465–473 (1980).
Schafer et al., *Monatshefte fur Chemie,* 109 527–535 (1978).

Primary Examiner—Donald G. Daus
Assistant Examiner—E. Bernhardt
Attorney, Agent, or Firm—Nancy S. Mayer; Janice E. Williams; Alan D. Lourie

[57] ABSTRACT

This invention relates to novel substituted 4-aminoquinoline derivatives which are inhibitors of gastric acid secretion in mammals. A compound of the invention is 3-butyryl-4-(2-methylphenylamino)-8-methoxyquinoline.

4 Claims, No Drawings

4-AMINO-3-CARBONYL SUBSTITUTED QUINOLINES AS INHIBITORS OF GASTRIC ACID SECRETION

This is a continuation of application Ser. No. 092,749 filed on Sept. 3, 1987.

COMPOUNDS

The present invention relates to novel substituted quinoline derivatives, processes for their preparation, intermediates useful in their preparation, pharmaceutical compositions containing them and their use in therapy.

Accordingly, the present invention provides, in a first aspect, a compound of structure (I):

[Structure I: 4-amino-3-carbonyl quinoline with $R^2$NH at 4-position, C(O)$R^1$ at 3-position, and $(R^3)_n$ on benzo ring]

in which $R^1$ is hydrogen, $C_{1-6}$alkyl, $C_{1-6}$alkoxy$C_{1-6}$alkyl, $C_{3-6}$cycloalkyl, $C_{3-6}$cycloalkyl$C_{1-6}$alkyl, phenyl, phenyl$C_{1-6}$alkyl, the phenyl groups being optionally substituted;

$R^2$ is $C_{1-6}$alkyl, $C_{3-6}$cycloalkyl, $C_{3-6}$cycloalkyl-$C_{1-6}$alkyl, phenyl, phenyl$C_{1-6}$alkyl or phenyl substituted by 1-3 radicals selected from $C_{1-6}$alkyl, $C_{1-6}$alkoxy, amino $C_{1-6}$alkylthio, halogen, cyano, hydroxy, carbamoyl, carboxy, $C_{1-6}$alkanoyl, trifluoromethyl and nitro;

$R^3$ is $C_{1-6}$alkyl, phenyl, $C_{1-6}$alkoxy, $C_{1-6}$alkylthio, $C_{1-6}$alkanoyl, amino, $C_{1-6}$alkylamino, di-$C_{1-6}$alkylamino, halogen, trifluoromethyl or cyano; and n is 0, 1 or 2, or a pharmaceutically acceptable salt thereof.

Suitably, $R^1$ is $C_{3-6}$cycloalkyl, $C_{3-6}$cycloalkyl$C_{1-6}$alkyl, phenyl, phenyl$C_{1-6}$alkyl, the phenyl groups being optionally substituted. Preferably $R^1$ is $C_{1-6}$alkyl. Most preferably $R^1$ is propyl, in particular n-propyl.

Preferably $R^2$ is a substituted phenyl group. More preferably, $R^2$ is a phenyl group substituted by a single substituent; in particular in the 2-position. Most preferably $R^2$ is a phenyl group substituted in the 2-position by a $C_{1-6}$alkyl or $C_{1-6}$alkoxy group, for example a methyl or methoxy group.

Suitably, n is 2 and one group $R^3$ is in the 8-position. Preferably n is 0; more preferably n is 1, and the group $R^3$ is in the 8-position.

Suitably $R^3$ is $C_{1-6}$alkylphenyl, $C_{1-6}$alkylthio, $C_{1-4}$alkanoyl, amino, $C_{1-6}$alkylamino, di$C_{1-6}$alkylamino, halogen, trifluoromethyl or cyano.

Preferably $R^3$ is hydrogen or $C_{1-6}$alkoxy, for example methoxy, or $C_{1-6}$alkyl, for example, methyl.

$C_{1-6}$alkyl groups (either alone or as part of another group) can be straight or branched.

Phenyl $C_{1-6}$alkyl groups include for example the phenylmethyl (benzyl), methylbenzyl, phenylethyl, phenylpropyl and phenylbutyl groups.

Substituted phenyl and phenyl $C_{1-6}$alkyl groups $R^1$ include, for example phenyl groups substituted by 1 to 3 substituents as hereinbefore described for substituted phenyl groups $R^2$.

It will be appreciated that compounds of structure (I) in which one or more of $R^1$ to $R^3$ is a $C_{3-6}$alkyl group (either alone or as part of another group for example a benzyl or phenethyl group) may contain an asymmetric centre due to the presence of the $C_{3-6}$alkyl group. Such compounds will exist as two (or more) optical isomers (enantiomers/diastereoisomers). Both the pure enantiomers, racemic mixtures (50% of each enantiomer) and unequal mixtures of the two are included within the scope of the present invention. Further, all diastereomeric forms possible (pure enantiomers and mixtures thereof) are within the scope of the invention.

Compounds of structure (I) can form pharmaceutically acceptable acid addition salts with suitable organic and inorganic acids the nature of which will be apparent to persons skilled in the art. For example, pharmaceutically acceptable salts can be formed by reaction with hydrochloric, sulphuric, or phosphoric acids; aliphatic, aromatic or heterocyclic sulphonic acids or carboxylic acids such as for example, citric, maleic or fumaric acids. In particular, salts formed with such carboxylic acids, especially citric acid, have improved solubility characteristics when compared to the parent compound.

In a further aspect, the present invention provides a process for the preparation of a compound of structure (I) which comprises (a) reaction of a compound of structure (II) with a compound of structure (III):

[Structure II: quinoline with X at 4-position, C(O)$R^1$ at 3-position, $(R^3)_n$ on benzo ring] $R^2$NH$_2$ (III)

in which $R^1$ and $R^2$ are as described for structure (I) and X is a group displaceable by an amine;

(b) for compounds of structure (I) in which $R^2$ is $C_{1-6}$alkyl, $C_{3-6}$cycloalkyl, $C_{3-6}$cycloalkyl$C_{1-6}$alkyl or phenyl$C_{1-6}$alkyl reaction of a compound of structure (IV) with a compound of structure (V)

[Structure IV: 4-amino-3-carbonyl quinoline with NH$_2$ at 4-position, C(O)$R^1$ at 3-position, $(R^3)_n$ on benzo ring] $R^{2'}X^1$ (V)

in which $R^1$, $R^3$ and n are as described for structure (I); $R^{2'}$ is $C_{1-6}$alkyl, $C_{3-6}$cycloalkyl, $C_{3-6}$cycloalkyl-$C_{1-6}$alkyl or phenyl$C_{1-6}$alkyl and $X^1$ is a leaving group;

(c) reduction of a compound of structure (VI)

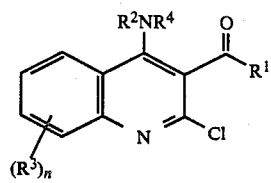

in which $R^1$, $R^2$, $R^3$ and n are as described for structure (I); and $R^4$ is hydrogen or a nitrogen protecting group;

(d) for compounds of structure (I) in which $R^1$ is $C_{2-6}$alkyl, $C_{3-6}$cycloalkyl$C_{1-6}$alkyl or optionally substituted phenyl$C_{1-6}$alkyl, alkylation of a compound of structure (VII)

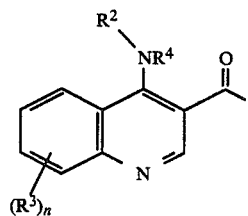

in which $R^2$, $R^3$ and n are as described for structure (I) and $R^4$ is hydrogen or a protecting group;

(e) oxidation of a compound of structure (VIII)

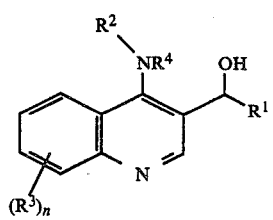

in which $R^1$, $R^2$, $R^3$ and n are as described for structure (I), and $R^4$ is hydrogen or a nitrogen protecting group; and thereafter if desired, removing any protecting groups;
converting a group $R^1$ into another group $R^1$;
forming a pharmaceutically acceptable salt.

Suitable groups X displaceable by an amine, include for example, aryl or alkylsulphonates, for example, toluene-p-sulphonate or methane sulphonate, alkylthio, alkylsulphonyl, alkylsulphinyl or alkoxy. Preferably X is a halo moiety, for example, chloro or bromo.

Suitable leaving groups $X^1$ will be apparent to those skilled in the art and include for example a halo moiety, preferably chloro or bromo.

Suitable nitrogen protecting groups $R^4$ will be apparent to those skilled in the art for example as described in "Protective Groups in Organic Synthesis" T. W. Greene, 1981 (Wiley).

The reaction between compounds of structure (II) and compounds of structure (III) is carried out in an organic solvent at a temperature of between ambient and reflux temperature of the solvent used. Suitable solvents include, for example, tetrahydrofuran, dioxan or anisole. Preferably the reaction is carried out at reflux temperature in dioxan as a solvent.

The reaction between compounds of structure (IV) and compounds of structure (V) is carried out in an organic solvent at a temperature of between ambient and reflux temperature of the solvent used, preferably in the presence of a base. Suitable solvents include for example, lower alkanols such as ethanol. Suitable bases include for example, tertiary amine bases such as triethylamine.

The reduction of a compound of structure (VI) is carried out by for example hydrogenation, over a noble metal catalyst in a suitable solvent. Suitably the reaction is carried out over a palladium on carbon catalyst in ethanol as a solvent.

The compounds of structure (VI) can be prepared from the corresponding compounds of structure (IX)

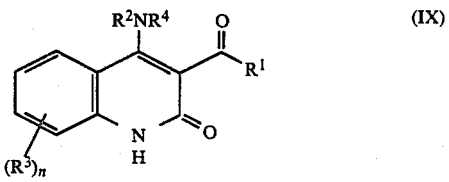

in which $R^1$, $R^2$, $R^3$, $R^4$ and n are as hereinbefore described, by reaction with, for example, phosphorus oxychloride.

The alkylation of a compound of structure (VII) is carried out in the presence of an alkylating agent in a suitable organic solvent at a temperature of between ambient and reflux temperature of the solvent used in the presence of a strong base. Suitable alkylating agents include, for example alkyl or aryl halides such as methyl or benzyliodide and dialkyl sulphonates such as dimethyl or diethylsulphate. Suitable strong bases include, for example, sodium hydride, lithium disopropylamine or dimsyl sodium (the sodium salt of dimethyl sulphoxide).

The oxidation of a compound of structure (VIII) is carried out in a suitable solvent in the presence of an oxidising agent. Suitable oxidising agents include, for example, manganese dioxide or chromium trioxide.

The intermediates of structure (II), (IV), (VI), (VIII) and (IX) can be prepared by standard techniques.

The intermediates of structure (III) and (V) are commercially available or can be prepared by standard techniques.

The compounds of structure (I) and their pharmaceutically acceptable salts exert an anti-secretory effect by inhibition of the gastrointestinal H+K+ATPase enzyme (Fellenius, E., Berglindh, T., Sachs, G., Olke, L., Elander, B., Sjostrand, S. E., and Wahlmark, B., 1981, Nature, 290, 159–61).

In further aspect therefore the present invention provides compounds of structure (I) and pharmaceutically acceptable salts thereof for use in therapy. The compounds of structure (I) and their pharmaceutically acceptable salts inhibit exogenously and endogenously stimulated gastric acid secretion and are useful in the treatment of gastrointestinal diseases in mammals, in particular humans. Such diseases include, for example, gastric and duodenal ulcers, aspiration pneumonitis and Zollinger-Ellison Syndrome.

Further, the compounds of structure (I) can be used in the treatment of other disorders where an anti-secretory effect is desirable for example in patients with gastritis, NSAID induced gastritis, acute upper intestinal bleeding, in patients with a history of chronic and excessive alcohol consumption, and in patients with gastro oesophageal reflux disease (GERD).

In therapeutic use, the compounds of the present invention are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The present invention also provides a method of inhibiting gastric acid secretion which comprises administering to a mammal in need thereof an effective amount of a compound of the formula (I) or a pharmaceutically acceptable salt thereof; and a method of treatment of diseases of the stomach or intestine based on increased acid secretion which comprises administering to a mammal in need thereof an effective amount of a compound of the formula (I) or a pharmaceutically acceptable salt thereof.

The pharmaceutically acceptable compounds of the invention will normally be administered to a subject for the treatment of gastro-intestinal diseases and other conditions caused or exacerbated by gastric acidity. The daily dosage regimen for an adult patient may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the formula (I) or a pharmaceutically acceptable salt thereof calculated as the free base, the compound being administered 1 to 4 times per day. Suitably the compounds will be administered for a period of continuous therapy, for example for a week or more.

In addition, the compounds of the present invention can be co-administered with further active ingredients, such as antacids (for example magnesium carbonate or hydroxide and aluminium hydroxide), non-steroidal anti-flammatory drugs (for example indomethacin, aspirin or naproxen), steroids, or nitrite scavengers (for example ascorbic acid or aminosulphonic acid), or other drugs used for treating gastric ulcers (for example pirenzipine, prostanoids for example 16,16 dimethyl $PGE_2$, or histamine $H_2$-antagonists (for example, cimetidine).

The following examples illustrate the invention. Temperatures are recorded in degrees centigrade.

EXAMPLE 1

Preparation of
3-Acetyl-4-(2-methylphenylamino)-8-methoxyquinoline

A. Preparation of ethyl 2-acetyl-3-(2-methoxyphenylamino)acrylate

A mixture of o-anisidine (113 ml, 1 mol), ethyl acetoacetate (127 ml, 1 mol) and triethyl orthoformate (166 ml, 1 mol) was heated such that ethanol distilled over slowly. After 2.5 hours the mixture was cooled, diluted with methanol (200 ml) and allowed to crystallise. The crude product was recrystallised from ethyl acetate/petroleum ether to give N-(2-methoxyphenyl)-2-acetyl-3-(2-methoxyphenylamino)acrylamide as a by-product. Evaporation of the mother liquors and recrystallisation from methanol gave ethyl 2-acetyl-3-(2-methoxyphenylamino)acrylate (49 g, 19%), m.p. 103°–105°.

B. Preparation of 3-acetyl-8-methoxy-4(1H)-quinolone

Ethyl 2-acetyl-3-(2-methoxyphenylamino)acrylate (48 g) was added in portions to boiling diphenyl ether (250 ml) and the mixture heated under reflux for 1 hour. The mixture was cooled and crystallised from a 1:1 mixture of ether and petroleum ether. The solid was filtered off and triturated with boiling ethanol to give 3-acetyl-8-methoxy-4(1H)-quinolone as a brown solid (12.1 g, 31%), m.p. 287°–289°.

C. Preparation of 3-acetyl-4-chloro-8-methoxyquinoline

3-Acetyl-8-methoxy-4(1H)-quinolone (4.23 g, 19 mmol) and phosphorus oxychloride (150 ml) were heated under reflux for 45 minutes, evaporated to small volume in vacuo, poured onto ice, and the mixture adjusted to pH 4 with sodium bicarbonate. Extraction with chloroform, drying and evaporation of the organic solution gave crude 3-acetyl-4-chloro-8-methoxyquinoline as a dark coloured oil (7.9 g), which was used without purification.

D. Preparation of 3-acetyl-4-(2-methylphenylamino)-8-methoxyquinoline

A mixture of crude 3-acetyl-4-chloro-8-methoxyquinoline (7.9 g) and o-toluidine (2 ml, 19 mmol) in dioxan (150 ml) was heated under reflux with stirring for 2 hours, then cooled and evaporated. Aqueous sodium bicarbonate was added, the mixture extracted with chloroform, and the organic extract dried and evaporated. Recrystallisation from ethyl acetate and then from ethanol gave 3-acetyl-4-(2-methylphenylamino)-8-methoxyquinoline (2.65 g, 44% from 3-acetyl-8-methoxy-4(1H)-quinolone), m.p. 171°–173°.

$C_{19}H_{18}N_2O_2$: Found C 74.77, H 5.89, N 9.15; Requires C 74.49, H 5.92, N 9.14.

EXAMPLE 2

Preparation of 3-Butyryl-4-(2-methylphenylamino)-8-methoxyquinoline

A. Preparation of ethyl 2-butyryl-3-(2-methoxyphenylamino)acrylate

A mixture of o-anisidine (22.6 ml, 0.2 mol), triethyl orthoformate (33.3 ml, 0.2 mol) and ethyl butyrylacetate (31.6 ml, 0.2 mol) was heated such that ethanol distilled over slowly. After 2.5 hours the mixture was allowed to cool, diluted with methanol (100 ml) and allowed to crystallise. The N-(2-methoxyphenyl)-2-butyryl-3-(2-methoxyphenylamino)acrylamide by-product was filtered off. Evaporation of the mother liquors and recrystallisation from petroleum ether (40–60) gave ethyl 2-butyryl-3-(2-methoxyphenylamino)acrylate (15.82 g, 27.2%), m.p. 74°–76°.

B. Preparation of 3-butyryl-8-methoxy-4(1H)-quinolone

Ethyl 2-butyryl-3-(2-methoxyphenylamino)acrylate (15.50 g, 0.053 mol) was added in portions to boiling diphenyl ether (400 ml) and the mixture heated under reflux for 1.5 hours. After cooling, the solution was diluted with ether and petroleum ether, filtered, and the solid washed with petroleum ether to give 3-butyryl-8-methoxy-4-(1H)-quinolone as light grey crystals (13.46 g, 63.1%, m.p. 200°–202°.

C. Preparation of 3-butyryl-4-chloro-8-methoxyquinoline

3-Butyryl-8-methoxy-4(1H)-quinolone (9.0 g, 0.037 mol) and phosphorus oxychloride (100 ml) were heated under reflux for 30 minutes. When cool, the mixture was poured onto ice, adjusted to pH 4 with sodium bicarbonate and extracted with dichloromethane. Evaporation and crystallisation from ethyl acetate-petroleum ether gave 3-butyryl-4-chloro-8-methoxyquinoline (5.5 g, 58.5%), m.p. 114°–116°.

D. Preparation of 3-butyryl-4-(2-methylphenylamino)-8-methoxyquinoline

A mixture of 3-butyryl-4-chloro-8-methoxyquinoline (6.0 g, 0.023 mol) and o-toluidine (6.0 ml, 0.056 mol) in 1,4-dioxan (100 ml) was heated under reflux with stirring for 1 hour. The mixture was evaporated and chromatographed (silica gel, 2% methanol in dichloromethane) to give 3-butyryl-4-(2-methylphenylamino)-8-methoxyquinoline as an oil which was isolated as the hydrochloride salt (2.12 g, 25.1%), m.p. 215°–217° by crystallisation from ethyl acetate and then recrystallisation from acetone.

$C_{21}H_{22}N_2O_2.HCl.0.08EtOAc$: Found C 67.76, H 6.31, N 7.41, Cl 9.38; Requires C 67.51, H 6.32, N 7.30, Cl 9.38.

EXAMPLE 2A

A. Preparation of ethyl 3-butyryl-4-(2-methoxyphenylamino)acrylate

A mixture of ethyl butyrylacetate (298 g, 1.88 mol), triethyl orthoformate (627 ml, 3.77 mol) and acetic anhydride (177 ml, 1.88 mol) was heated at reflux for 5 hours, then the volatile components evaporated in vacuo. 2-Methylaniline (212 ml, 1.88 mol) was added, the mixture heated to reflux, allowed to cool partially, and poured into high boiling petroleum ether. Filtration and washing with petroleum ether gave ethyl 3-butyryl-4-(2-methoxyphenylamino)acrylate (178 g, 32%). A further 173 g (32%) of 3-butyryl-4-(2-methoxyphenylamino)acrylate could be obtained from the mother liquors by evaporation, dissolution in ethyl acetate, acid wash and trituration with petroleum ether.

EXAMPLE 3

Preparation of 3-hexanoyl-4-(2-methylphenylamino)-8-methoxyquinoline

A. Preparation of ethyl 3-(2-methoxyphenylamino)acrylate o-Anisidine (57 ml, 0.5 mol) and ethyl propiolate (51 ml, 0.5 mol) were heated together under reflux in ethanol (200 ml) for 3 hours. The solvent was evaporated to afford ethyl 3-(2-methoxyphenylamino)acrylate as a yellow oil (55 g, 100%).

B. Preparation of ethyl 2-hexanoyl-3-2-methoxyphenylamino)acrylate

50% Sodium hydride (4.8 g, 0.1 mol) was washed with petroleum ether and then suspended under nitrogen in dry tetrahydrofuran (50 ml) at −30° C. Ethyl 3-(2-methoxyphenylamino)acrylate (17.4 g, 0.1 mol) in dry tetrahydrofuran (100 ml) was added dropwise to the stirred suspension keeping the temperature below −20° C. Cooling was removed and the mixture was stirred until a deep red colour was obtained. The mixture was re-cooled to −30° C. and hexanoyl chloride (13.8 ml, 0.1 mol) in dry tetrahydrofuran (50 ml) was added dropwise. Cooling was again removed and the mixture was stirred for 2 hours. The mixture was partitioned between 10% hydrochloric acid and dichloromethane then washed with water and brine, dried and evaporated to afford an oil which was chromatographed (silica gel, chloroform) to give ethyl 2-hexanoyl-3-(2-methoxyphenyl-amino)acrylate, (20 g, 62.7%).

C. Preparation of 3-hexanoyl-8-methoxy-4-(1H)-quinolone

Ethyl 2-hexanoyl-3-(2-methoxyphenylamino)acrylate (18 g, 0.056 mol) was added in portions to boiling diphenyl ether (200 ml) and the mixtrue heated under reflux for 1 hour. After cooling, the mixture was diluted with petroleum ether, filtered and the solid washed with petroleum ether to give 3-hexanoyl-8-methoxy-4(1H)-quinolone (5.2 g, 33.8%), m.p. 169°–71° C.

D. Preparation of 4-chloro-3-hexanoyl-8-methoxyquinoline 3-hexanoyl-8-methoxy-4(1H)-quinolone (4.6 g, 0.017 mol) was heated under reflux in a mixture of phosphorus oxychloride (8 ml) and chloroform (50 ml) for 1.5 hours. When cool, the mixture was poured into a vigorously stirred mixture of sodium hydrogen carbonate solution, ice and chloroform. The layers were separated and the organic solution was washed with sodium hydrogen carbonate solution and brine. Evaporation of the chloroform solution afforded 4-chloro-3-hexanoyl-8-methoxyquinoline as a yellow-brown oil (5 g).

E. Preparation of 3-hexanoyl-4-(2-methylphenylamino)-8-methoxyquinoline 3-hexanoyl-4-chloro-8-methoxyquinoline (5 g, 0.071 mol) and o-toluidine (2 ml, 0.019 mol) were heated under reflux in 1,4-dioxan (50 ml) for 1 hour. The solvent was evaporated and the residue was taken up in dichloromethane, washed with 10% hydrochloric acid, water, sodium hydrogen carbonate solution and brine, dried and evaporated. Trituration with ethyl acetate/ether and recrystallisation from methanol-water gave 3-hexanoyl-4-(2-methylphenylamino)-8-methoxyquinoline as yellow needles (2.53 g, 45.3%), mp 94°-6° C.

$C_{23}H_{26}N_2O_2$: Found C 76.29, H 7.12, N 7.59; Requires C 76.21, H 7.23, N 7.73.

EXAMPLE 4

Preparation of 3-cyclohexylcarbonyl-4-(2-methylphenylamino)-8-methoxyquinoline

A. Preparation of ethyl 2-cyclohexylcarbonyl-3-(2-methylphenylamino)acrylate

50% Sodium hydride (4.8 g, 0.1 mol) was washed with petroleum ether then stirred in dry tetrahydrofuran (50 ml) under nitrogen at −20° C. Ethyl 3-(2-methoxyphenylamino)acrylate (17.4 g, 0.1 mol) in dry tetrahydrofuran (100 ml) was added dropwise, keeping the temperature to −20° C. Cooling was removed and the mixture was stirred until a dark red colour was achieved. The mixture was recooled to −20° C. and cyclohexylcarbonyl chloride (14.0 ml, 0.1 mol) in dry tetrahydrofuran (50 ml) was added dropwise. The mixture was allowed to warm to room temperature and was stirred for a further 3 hours. The solvent was evaporated and the residue was partitioned between dichloromethane and 2M HCl. The organic layer was washed with water and brine, dried and evaporated to an oil which was chromatographed (silica gel, dichloromethane-hexane) to afford ethyl 2-cyclohexylcarbonyl-3-(2-methoxyphenylamino)acrylate as a yellow oil (23.3 g, 70%).

B. Preparation of 3-cyclohexylcarbonyl-8-methoxy-4(1H)quinolone

Ethyl 2-cyclohexylcarbonyl-3-(2-methoxyphenylamino)acrylate (20 g, 0.06 mol) was added in portions to boiling diphenyl ether (200 ml) and the mixture was heated under reflux for 1.5 hours. When cool, the mixture was diluted with petroleum ether and allowed to crystallise overnight to give 3-cyclohexylcarbonyl-8-methoxy-4(1H)-quinolone (6.0 g, 35.2%), m.p. 168°-70° C.

C. Preparation of 4-chloro-3-cyclohexylcarbonyl-8-methoxyquinoline

3-Cyclohexylcarbonyl-8-methoxy-4(1H)-quinolone (5.8 g, 0.02 mol) was heated under reflux in a mixture of chloroform (100 ml) and phosphorus oxychloride (15 ml) for 2.5 hours. The reaction mixture was partitioned between chloroform, ice and sodium hydrogen carbonate solution (100 g in 1.5 l) and the organic solution was washed with sodium hydrogen carbonate solution and brine. The chloroform solution was dried and evaporated to give 4-chloro-3-cyclohexylcarbonyl-8-methoxy-quinoline (5.5 g, 90%) as an oil.

D. Preparation of 3-cyclohexylcarbonyl-4-(2-methylphenylamino)-8-methoxyquinoline 3-cyclohexylcarbonyl-4-chloro-8-methoxyquinoline (5.0 g, 0.017 mol) was heated under reflux in a mixture of 1,4-dioxan (50 ml) and o-toluidine (2.0 ml) for 2 hours. The reaction mixture was evaporated and the residue dissolved in dichloromethane, washed with sodium hydrogen carbonate solution and brine. The organic solution was dried, evaporated and chromatographed (silica gel, dichloromethane) to affort an oil, which on trituration with hexane-ether gave 3-cyclohexylcarbonyl-4-(2-methylphenylamino)-8-methoxyquinoline as yellow crystals (0.58 g, 9.4%) m.p. 115°-7° C.

$C_{24}H_{26}N_2O_2$: Found: C 76.66, H 7.02, N 7.37; Requires: C 76.98, H 7.00, N 7.48.

EXAMPLE 5

Preparation of 3-benzoyl-4-(2-methoxyphenylamino)-8-methoxyquinoline

A. Preparation of ethyl 2-benzoyl-3-(2-methoxyphenylamino)acrylate

50% Sodium hydride (2.4 g, 0.05 mol) was washed with petroleum ether, suspended in dry toluene (50 ml) and stirred at 5° C. Ethyl 3-(2-methoxyphenylamino)acrylate (8.7 g, 0.05 mol) in dry toluene (25 ml) was added and the mixture was stirred for 2.5 hours. Benzoyl chloride (6.8 g, 0.05 mol) in dry toluene (25 ml) was added dropwise and the mixture was heated under reflux for 2 hours. The mixture was cooled, washed with dilute hydrochloric acid, water and brine, then dried and evaporated. The residue was chromatographed (silica gel, dichloromethane) to afford ethyl 2-benzoyl-3-(2-methoxyphenylamino)acrylate (7.62 g, 46.8%) as a yellow oil.

B. Preparation of 3-benzoyl-8-methoxy-4(1H)-quinolone

Ethyl 2-benzoyl-3-(2-methoxyphenylamino)acrylate (6.0 g, 0.018 mol) was added in portions to boiling diphenyl ether (100 ml) and heated under reflux for 45 minutes. The reaction mixture was allowed to cool and diluted with petroleum ether to afford the crystalline 3-benzoyl-8-methoxy-4(1H)-quinolone (4.7 g, 91%).

C. Preparation of 3-benzoyl-4-chloro-8-methoxyquinoline

3-Benzoyl-8-methoxy-4(1H)-quinolone (3.2 g, 0.011 mol) was heated under reflux in a mixture of chloroform (50 ml) and phosphorus oxychloride (7 ml) for 45 minutes. The mixture was cooled and poured into a stirred mixture of sodium hydrogen carbonate solution, ice and chloroform. The organic phase was separated, washed with sodium hydrogen carbonate solution, water and brine. The dried solution was filtered and evaporated to afford 3-benzoyl-4-chloro-8-methoxyquinoline as a yellow oil (3.5 g, 100%).

D. Preparation of 3-benzoyl-4-(2-methoxyphenylamino)-8-methoxyquinoline 3-Benzoyl-4-chloro-8-methoxyquinoline (2.8 g, 0.0094 mol) was heated under reflux in a mixture of 1,4-dioxan (50 ml) and o-anisidine (7 ml) for 1 hour. The solvent was evaporated and the residue was dissolved in dichloromethane, and washed with dilute hydrochloric acid, sodium hydrogen carbonate solution, water and brine. The organic solution was dried and evaporated to an oil which was chromatographed (silica gel, 1% methanol in dichloromethane) to give an oil which afforded yellow crystals of 3-benzoyl-4-(2-methoxyphenylamino)-8-methoxyquinoline (2.2 g, 61%) from ethyl acetate, m.p. 200°-202°.

$C_{24}H_{20}N_2O_3$: Found C 74.95, H 5.22, N 7.10; Requires C 74.98, H 5.24, N 7.29.

EXAMPLE 6

Preparation of 3-benzoyl-4-(2-methylphenylamino)-8-methoxyquinoline

3-Benzoyl-4-chloro-8-methoxyquinoline (3.0 g, 0.01 mol) was heated under reflux in 1,4-dioxan (100 ml)

with o-toluidine (5.0 ml) for 1 hour. The solvent was evaporated and the residue was dissolved in dichloromethane, and washed with dilute hydrochloric acid, sodium hydrogen carbonate solution, water and brine. The organic solution was dried and evaporated to an oil which was chromatographed (silic gel, 1% methanolic ammonia in dichloromethane). 3-Benzoyl-4-(2-methylphenylamino)-8-methoxyquinoline was isolated as crystals (0.95 g, 25.8%) from ether/hexane, m.p. 128–130.

$C_{24}H_{20}N_2O_2$: Found C 78.11, H 5.32, N 7.42; Requires C 78.24, H 5.47, N 7.60.

EXAMPLE 7

Preparation of 3-methoxyacetyl-4-(2-methylphenylamino)-8-methoxyquinoline

A. Preparation of methyl 2-methoxyacetyl-3-(2-methoxyphenylamino)acrylate

Methyl 4-methoxyacetoacetate (43 ml, 0.33 mol), acetic anhydride (31 ml, 0.33 mol) and triethyl orthoformate (110 ml, 0.66 mol) were heated under reflux for 2 hours, then the excess triethyl orthoformate and the produced ethyl acetate were evaporated from the mixture under reduced pressure. o-Anisidine (43 ml, 0.35 mol) was added and ethanol (15 ml) was distilled over under atmospheric pressure. When cool, the mixture was poured slowly into hexane to produce methyl 2-methoxyacetyl-3-(2-methoxyphenylamino)acrylate (55 g, 59.5%).

B. Preparation of 3-methoxyacetyl-8-methoxy-4(1H)-quinolone

Methyl 2-methoxyacetyl-3-(2-methoxyphenylamino)acrylate (55 g, 0.2 mol) was added in portions to boiling diphenyl ether (500 ml) and the mixture was heated under reflux for 45 minutes. The mixture was allowed to cool and diluted with petroleum ether to afford 3-methoxyacetyl-8-methoxy-4(1H)-quinolone (40 g, 82.5%) as light brown crystals.

C. Preparation of 4-chloro-8-methoxy-3-methoxyacetylquinoline

3-Methoxyacetyl-8-methoxy-4-(1H)-quinolone (39 g, 0.16 mol) was heated under reflux in a mixture of phosphoryl chloride (150 ml) and chloroform (200 ml) for 45 minutes. The solvent was evaporated and the mixture ws partitioned between chloroform and sodium hydrogen carbonate solution. The aqueous layer was separated and extracted with chloroform. The combined organic solutions were washed with sodium hydrogen carbonate solution and brine. Evaporation gave an oil which afforded yellow crystals of 4-chloro-8-methoxy-3-methoxyacetylquinoline (19.2 g, 45.8%), m.p. 96°–8°.

D. Preparation of 3-methoxyacetyl-4-(2-methylphenylamino)-8-methoxyquinoline 3-methoxyacetyl-4-chloro-8-methoxyquinoline (19.0 g, 0.07 mol) and o-toluidine (9.0 ml, 0.08 mol) were heated under reflux in 1,4-dioxan (250 ml) for 1 hour. The solvent was removed and the residue taken up in dichloromethane, washed with dilute hydrochloric acid, sodium hydrogen carbonate solution, and brine. Evaporation of the solvent gave an oil, which afforded 8-methoxy-3-methoxymethylcarbonyl-4-(2-methylphenylamino)quinoline (19.5 g, 81%) as yellow crystals from ether, m.p. 122°–3°.

$C_{20}H_{20}N_2O_3$: Requires C 71.41, H 5.99, N 8.33; Found C 71.10, H 5.85, N 8.27.

EXAMPLE 8

Preparation of 3-isobutyryl-4-(2-methylphenylamino)-8-methoxyquinoline

A. Preparation of ethyl 2-isobutyryl-3-(2-methoxyphenylamino)acrylate

50% Sodium hydride (4,8 g, 0.1 mol) was washed with petroleum ether and suspended in dry tetrahydrofuran (50 ml) under nitrogen at −10° C. Ethyl 3-(2-methoxyphenylamino)acrylate (22.4 g, 0.1 mol) in dry tetrahydrofuran (70 ml) was added dropwise to the suspension keeping the temperature to below 0° C. Cooling ws removed and the mixture was stirred at ambient temperature until a deep orange colour was obtained. The mixture was recooled to −20° C. and treated dropwise with a solution of isobutyryl chloride (11.0 ml, 0.11 mol) in dry tetrahydrofuran (30 ml). The cooling bath was again removed, and the mixture stirred overnight at room temperature. The solvent was evaporated and the residue was dissolved in dichloromethane and washed with dilute hydrochloric acid and brine, dried, filtered and evaporated. The crude product was chromatographed (silica gel, petroleum ether/dichloromethane) to afford ethyl 2-isobutyryl-3-(2-methoxyphenylamino)acrylate as an oil (22.6 g, 77.5%).

B. Preparation of 3-isobutyryl-8-methoxy-4(1H)-quinolone

Ethyl 2-isobutyryl-3-(2-methoxyphenylamino)acrylate (18.8 g, 0.065 mol) was added in portions to boiling diphenyl ether (150 ml). The mixture was heated under reflux for 30 minutes, cooled, and diluted with petroleum ether (500 ml). Filtration of the mixture gave 3-isobutyryl-8-methoxy-4(1H)-quinolone as a light brown solid (8.32 g, 52.2%).

C. Preparation of 4-chloro-3-isobutyryl-8-methoxyquinoline

3-Isobutyryl-8-methoxy-4(1H)-quinolone (8.31 g, 0.034 mol) was heated under reflux in a mixture of phosphorus oxychloride (20 ml) and chloroform (30 ml) for 30 minutes. The mixture was evaporated and the residue was partitioned between dichloromethane and sodium hydrogen carbonate solution. The organic solution was washed with sodium hydrogen carbonate solution, water and brine, dried, filtered and evaporated to give 4-chloro-3-isobutyryl-8-methoxyquinoline as a brown oil (6.4 g, 71%).

D. Preparation of 3-isobutyryl-4-(2-methylphenylamino)-8-methoxyquinolone 3-isobutyryl-4-chloro-8-methoxyquinoline (6.0 g, 0.022 mol) and o-toluidine (6 ml, 0.055 mol) were heated in 1,4-dioxan (100 ml) for 45 minutes. The solvent was evaporated and the residue was dissolved in dichloromethane, washed with dilute hydrochloric acid, sodium hydrogen carbonate solution and brine. The solution was dried and evaporated to an oil, which was chromatographed (silica gel, dichloromethane) to afford a yellow oil. Trituration in ether gave yellow crystals of 3-isobutyryl-4-(2-methylphenylamino)-8-methoxyquinoline (1.41 g, 18.3%), m.p. 116°–8°.

$C_{21}H_{22}N_2O_2$: Requires C 75.42, H 6.63, N 8.38; Found C 75.41, H 6.48, N 8.39.

EXAMPLE 9

Preparation of 3-butyryl-4-(2-methoxyphenylamino)-8-methoxyquinoline

3-Butyryl-4-chloro-8-methoxyquinoline (20.2 g, 0.077 mol) and o-anisidine (15 ml, 0.11 mol) were heated under reflux in 1,4-dioxan (150 ml) for 1 hour. The solvent was evaporated and the residue dissolved in dichloromethane and washed with dilute hydrochloric acid, sodium bicarbonate solution and brine. The solution was dried, filtered and evaporated to a yellow solid, which was triturated with ether to give 3-butyryl-4-(2-methoxyphenylamino)-8-methoxyquinoline (18.55 g, 68.75%) m.p. 159°–161°.

$C_{22}H_{24}N_2O_3.0.05CH_2Cl_2$: Requires C 71.29, H 6.28, N 7.90; Found C 71.11, H 6.28, N 7.88.

EXAMPLE 10

Preparation of 3-butyryl-4-(4-methoxy-2-methylphenylamino)-8-methoxyquinoline

3-Butyryl-4-chloro-8-methoxyquinoline (5.0 g, 0.019 mol) and 4-methoxy-2-methylaniline (3.0 g, 0.022 mol) were heated under reflux in 1,4-dioxan (50 ml) for 30 minutes. The solvent was evaporated and the residue was dissolved in dichloromethane, washed with dilute hydrochloric acid, sodium bicarbonate solution, water and brine. The solution was dried and evaporated to an oil, which crystallised on standing. The crystals were triturated with ether and recrytallised from ethyl acetate to give 3-butyryl-4-(4-methoxy-2-methylphenylamino)-8-methoxyquinoline (2.4 g, 34.8%), m.p. 161°–3°.

$C_{22}H_{24}N_2O_3$: Requires C 72.50, H 6.64, N 7.69; Found C 72.31, H 6.57, N 7.74.

EXAMPLE 11

Preparation of 3-butyryl-4-(2-methylphenylamino)-8-methylquinoline

A. Preparation of ethyl 2-butyryl-3-(2-methylphenylamino)acrylate

A mixture of ethyl butyrylacetate (100 g, 0.63 mol), triethyl orthoformate (210 ml, 1.26 mol) and acetic anhydride (60 ml, 0.63 mol) was heated under reflux for 6 hours, then excess triethyl orthoformate evaporated in vacuo. 2-Methyl aniline (67 ml, 0.63 mol) was added to the residue, the mixture heated at reflux for 30 minutes, then poured into petroleum ether. Filtration and washing gave ethyl 2-butyryl-3-(2-methylphenylamino)acrylate (67 g, 38%) as a mixture of E and Z isomers. The mother liquors were evaporated, taken up in ethyl acetate, washed with dilute hydrochloric acid, dried, evaporated and triturated with petroleum ether to give a further 57 g (33%) of ethyl 2-butyryl-3-(2-methylphenylamino)-acrylate.

B. Preparation of 3-butyryl-8-methyl-4(1H)-quinolone

Ethyl 2-butyryl-3-(2-methylphenylamino)acrylate (66 g, 0.24 mol) was added in portions to boiling diphenyl ether (500 ml), then heated at reflux for 1.5 hours. After partial cooling, the mixture was poured into high boiling petroleum ether. Filtration and washing with petroleum ether gave 3-butyryl-8-methyl-4(1H)-quinolone (54 g) as a pale solid, which was used without further purification.

C. Preparation of 3-butyryl-4-chloro-8-methylquinoline

3-Butyryl-8-methyl-4(1H)-quinolone (20 g) and phosphoryl chloride (80 ml) were heated under reflux for 45 minutes. Excess phosphoryl chloride was evaporated in vacuo, the residue poured onto ice and neutralised with sodium hydrogen carbonate. Extraction with dichloromethane, drying and evaporation gave 3-butyryl-4-chloro-8-methylquinoline (20 g) as a brown oil, which solidified at −15° C. but melted below room temperature. This was used without further purification.

D. Preparation of 3-butyryl-4-(2-methylphenylamino)-8-methylquinoline

3-Butyryl-4-chloro-8-methylquinoline (4.95 g, 20 mmol), 2-methylaniline (4.27 ml, 40 mmol) and tetrahydrofuran (20 ml) were heated at reflux for 30 minutes, the solvent evaporated and the residue triturated with ethyl acetate/ethanol. The hydrochloride salt was filtered off, converted to free base and recrystallised from ethyl acetate/petroleum ether then from aqueous methanol, to give 3-butyryl-4-(2-methylphenylamino)-8-methylquinoline (1.3 g), m.p. 110°–112°.

EXAMPLE 12

Preparation of 3-butyryl-4-(2-methoxyphenylamino)-8-methylquinoline

3-Butyryl-4-chloro-8-methylquinoline (4.95 g, 20 mmol), 2-methoxyaniline (4.51 ml, 40 mmol) and tetrahydrofuran (20 ml) were stirred at room temperature overnight. The hydrochloride salt was filtered off, converted to free base and recrystallised from ethyl acetate/petroleum ether to give 3-butyryl-4-(2-methoxyphenylamino)-8-methylquinoline (2.25 g), m.p. 135°–137°.

EXAMPLE 13

Preparation of 3-butyryl-4-(4-methoxy-2-methylphenylamino)-8-methylquinoline

3-Butyryl-4-chloro-8-methylquinoline (4.95 g, 20 mmol), 4-methoxy-2-methylaniline (5.15 ml, 40 mmol) and 1,4-dioxan (20 ml) were heated at reflux for 1 hour, the solvent evaporated, the residue taken up in dichloromethane, washed with aqueous sodium bicarbonate, dried and evaporated. Recrystallisation from methanol gave 3-butyryl-4-(4-methoxy-2-methylphenylamino)-8-methylquinoline (5.30 g), m.p. 114°–115°.

EXAMPLE 14

Preparation of 3-butyryl-4-(2,4-dimethoxyphenylamino)-8-methylquinoline

3-Butyryl-4-chloro-8-methylquinoline (2.48 g, 10 mmol), 2,4-dimethoxyaniline (3.06 g, 20 mmol) and 1,4-dioxan (20 ml) were heated at reflux for 1.5 hours, the solvent evaporated, the residue taken up in dichloromethane, washed with aqueous sodium bicarbonate, dried and evaporated. Chromatography (silica gel, 1% methanol in chloroform), conversion to the hydrochloride salt and recrystallisation from aqueous methanol gave 3-butyryl-4-(2,4-dimethoxyphenylamino)-8-methylquinoline hydrochloride (2.10 g, 57%), m.p. 190°–192°.

EXAMPLE 15

Preparation of 3-butyryl-4-(2,5-dimethoxyphenylamino)-8-methylquinoline

3-Butyryl-4-chloro-8-methylquinoline (2.48 g, 10 mmol), 2,5-dimethoxyaniline (3.06 g, 20 mmol) and 1,4-dioxan (10 ml) were stirred at room temperature overnight then heated at reflux for 30 minutes. The hydrochloride salt was filtered off, converted to free base and recrystallised from aqueous ethanol to give 3-butyryl-4-(2,5-dimethoxyphenylamino)-8-methylquinoline (1.07 g), m.p. 115°–116°.

$C_{22}H_{24}N_2O_3.0.1H_2O$: Found C 72.20, H 6.69, N 7.67; Requires C 72.15, H 6.66, N 7.65.

EXAMPLE 16

Preparation of 3-butyryl-4-(2-fluorophenylamino)-8-methylquinoline

3-Butyryl-4-chloro-8-methylquinoline (2.48 g, 10 mmol), 2-fluoroaniline (1.45 ml, 15 mmol) and 1,4-dioxan (10 ml) were stirred at room temperature overnight then heated at reflux for 30 minutes. The hydrochloride salt was filtered off, converted to free base and recrystallised from aqueous ethanol to give 3-butyryl-4-(2-fluorophenylamino)-8-methylquinoline (2.21 g), m.p. 109°–111°.

EXAMPLE 17

Preparation of 3-butyryl-4-(2-ethylphenylamino)-8-methylquinoline

3-Butyryl-4-chloro-8-methylquinoline (2.48 g, 10 mmol), 2-ethylaniline (1.85 ml, 15 mmol) and 1,4-dioxan (10 ml) were stirred at room temperature overnight then heated at reflux for 30 minutes. The solvent was evaporated, the residue converted to free base and recrystallised from aqueous ethanol to give 3-butyryl-4-(2-ethylphenylamino)-8-methylquinoline (2.38 g), m.p. 117°–119°.

EXAMPLE 18

Preparation of 3-butyryl-4-(2,4-dichlorophenylamino)-8-methylquinoline

3-Butyryl-4-chloro-8-methylquinoline (2.48 g, 10 mmol), 2,4-dichloroaniline (2.43 g, 15 mmol) and 1,4-dioxan (10 ml) were stirred at room temperature overnight then heated at reflux for 30 minutes. The hydrochloride salt was filtered off, converted to free base, triturated with ethanol and recrystallised from ethyl acetate to give 3-butyryl-4-(2,4-dichlorophenylamino)-8-methylquinoline (2.26 g), m.p. 169°–170°.

EXAMPLE 19

Preparation of 3-butyryl-4-(2,6-dimethylphenylamino)-8-methylquinoline

3-Butyryl-4-chloro-8-methylquinoline (2.48 g, 10 mmol) and 2,6-dimethylaniline (1.85 ml, 15 mmol) in dioxan (10 ml) were heated at reflux for 30 minutes, then the solvent evaporated and the product converted to free base. Recrystallisation from aqueous ethanol gave 3-butyryl-4-(2,6-dimethylphenylamino)-8-methylquinoline, m.p. 100°–101°.

EXAMPLE 20

Preparation of 3-butyryl-4-(2-chlorophenylamino)-8-methylquinoline

3-Butyryl-4-chloro-8-methylquinoline (2.48 g, 10 mmol) and 2-chloroaniline (1.6 ml, 15 mmol) in dioxan (10 ml) were heated at reflux for 30 minutes, then allowed to cool. The product was filtered off, converted to free base, and recrystallised from methanol to give 3-butyryl-4-(2-chlorophenylamino)-8-methylquinoline (1.53 g), m.p. 130°–131°.

EXAMPLE 21

Preparation of 3-butyryl-4-(4-chloro-2-methylphenylamino)-8-methylquinoline

3-Butyryl-4-chloro-8-methylquinoline (1.24 g, 5 mmol) and 4-chloro-2-methylaniline (1.06 g, 7.5 mmol) in dioxan (5 ml) were heated at reflux for 30 minutes, then allowed to cool. The product was filtered off, converted to free base, and recrystllised from methanol, to give 3-butyryl-4-(4-chloro-2-methylphenylamino)-8-methylquinoline (0.73 g), m.p. 166°–167°.

EXAMPLE 22

Preparation of 3-butyryl-4-(2-methoxy-5-methylphenylamino)-8-methylquinoline

3-Butyryl-4-chloro-8-methylquinoline (1.77 g, 7.14 mmol) and 2-methoxy-5-methylaniline (1.47 g, 10.7 mmol) in dioxan (10 ml) were heated at reflux for 30 minutes, then evaporated and converted to free base. Recrystallisation from methanol and then from ethyl acetate/petroleum ether gave 3-butyryl-4-(2-methoxy-5-methylphenylamino)-8-methylquinoline (1.32 g), m.p. 136°–138°.

EXAMPLE 23

Preparation of 3-butyryl-4-(2-methylphenylamino)quinoline

A. Preparation of ethyl 2-butyryl-3-ethoxyacrylate

A mixture of ethyl butyrylacetate (100 g, 0.63 mol), triethyl orthoformate (210 ml, 1.26 mol) and acetic anhydride (60 ml, 0.63 mol) was heated under reflux for 6 hours, then excess triethyl orthoformate evaporated in vacuo. The residue consisted mainly of ethyl 2-butyryl-3-ethoxyacrylate as a mixture of E and Z isomers, and was used without further purification.

B. Preparation of ethyl 2-butyryl-3-(phenylamino)acrylate

A mixture of ethyl 2-butyryl-3-ethoxyacrylate (95 g, 0.4 mol) and aniline (36 ml, 0.4 mol) was heated at reflux for 30 minutes, then cooled, diluted with petroleum ether, and left to crystallise at −20° overnight. Filtration and washing gave ethyl 2-butyryl-3-(phenylamino)acrylate (72 g, 60%) as a mixture of E and Z isomers.

C. Preparation of 3-butyryl-4(1H-quinolone

Ethyl 2-butyryl-3-(phenylamino)acrylate (70 g, 0.27 mol) was added in portions to boiling diphenyl ether (500 ml), then heated at reflux for 1.5 hours. After partial cooling, the mixture was poured into high boiling petroleum ether. Filtration and washing with petroleum ether gave 3-butyryl-4(1H)-quinolone (47 g) as a pale solid, which was used without further purification.

D. Preparation of 3-butyryl-4-chloroquinoline

3-Butyryl-4(1H)-quinolone (21.5 g) and phosphoryl chloride (80 ml) were heated under reflux for 45 minutes. Excess phosphoryl chloride was evaporated in vacuo, the residue poured onto ice and neutralised with sodium hydrogen carbonate. Extraction with dichloromethane, drying and evaporation gave 3-butyryl-4-chloroquinoline (22 g) as a brown oil, which solidified on standing. This was used without further purification.

E. Preparation of 3-butyryl-4-(2-methylphenylamino)quinoline

3-Butyryl-4-chloroquinoline (2.33 g, 10 mmol), 2-methylaniline (1.60 ml, 15 mmol) and dioxan (10 ml) were heated at reflux for 30 minutes, then allowed to cool. The hydrochloride salt was filtered off, converted to free base and recrystallised from aqueous ethanol to give 3-butyryl-4-(2-methylphenylamino)quinoline (1.80 g), m.p. 107°–109°.

EXAMPLE 24

Preparation of 3-butyryl-4-(2-methoxyphenylamino)quinoline

3-Butyryl-4-chloro-8-methylquinoline (2.33 g, 10 mmol), 2-methoxyaniline (1.69 ml, 15 mmol) and dioxan (10 ml) were heated at reflux for 30 minutes, then allowed to cool. The hydrochloride salt was filtered off, converted to free base and recrystallised from ethanol to give 3-butyryl-4-(2-methoxy-phenylamino)quinoline (2.78 g), m.p. 167°–168°.

EXAMPLE A

A tablet for oral administration is prepared by combining

|  | Mg/Tablet |
| --- | --- |
| Compound of structure (I) | 100 |
| Mannitol | 153 |
| Starch | 33 |
| crospovidone | 12 |
| microcrystalline cellulose | 30 |
| magnesium stearate | 2 |
|  | 330 mg | into a 9 mm tablet.

EXAMPLE B

An injection for parenteral administration was prepared from the following

| Compound of Example 2 | 6.68% (w:v) |
| --- | --- |
| 1 M citric acid | 30% (v:v) |
| sodium hydroxide (qs) | to pH 3.2 |
| water for injection EP to | 100 ml |

The compound of Example 2 was dissolved in the citric acid and the pH slowly adjusted to pH 3.2 with the sodium hydroxide solution. The solution was then made up to 100 ml with water, sterilised by filtration and sealed into appropriately sized ampoules and vials.

BIOLOGICAL DATA (A) $H^+K^+$ATPase Activity

The effects of a single high concentration (100 $\mu$M) of a compound of structure (I) on K-stimulated ATPase activity in lyophilised gastric vesicles was determined. Preferred compounds of structure (I) were also tested over a range of concentrations to determine IC$_{50}$ values.

(i) Preparation of lyophilised gastric vesicles (H/K-ATPase)

Lyophilised gastric vesicles were prepared from pig fundic mucosa after the method of Keeling et. al. (Biochem. Pharmacol., 34, 2967, 1985).

(ii) $K^+$-stimulated ATPase activity $K^+$-stimulated ATPase activity was determined at 37° C. in the presence of the following: 10 mM Pipes/Tris buffer pH 7.0, 2 mM MgSO$_4$, 1 mM KCL, 2 mM Na$_2$ATP and 3 $\mu$g protein/ml lyophilised gastric vesicles. After incubation for 30 minutes, the inorganic phosphate hydrolysed from ATP was determined by the method of Yoda and Hokin (Biochem. Biophys. Res. Commun. 40, 880, 1970).

Compounds of structure (I) were dissolved in dimethylsulphoxide which up to the highest concentration used had no effect on $K^+$-stimulated ATPase activity.

The effect of the highest concentration of each compound of structure (I) on the recovery of a standard amount of inorganic phosphate was also determined.

(iii) Results

The compounds of examples 1 to 4 and 6 to 10 gave IC$_{50}$ values in the range of from 1.05 to 16 $\mu$M.

(B) Aminopyrine (AP) accumulation in intact gastric vesicles

The effects of a single high concentration (100 $\mu$M) of a compound of structure (I) on AP accumulation in intact gastric vesicles was determined. Preferred compounds of structure (I) were also tested over a range of concentrations to determine IC$_{50}$ values.

(i) Preparation of intact gastric vesicles

Intact gastric vesicles were prepared from pig fundic mucosa after the method of Keeling et. al. (Biochem. Pharmacol., 34, 2967, 1985), except that material from the Ficoll/sucrose layer of the discontinuous density gradient was not recentrifuged and lyophilised, but was mixed with an equal volume of 60% sucrose and was stored at $-70°$ C.

(ii) AP accumulation

Test compound was incubated with intact gastric vesicles (25 $\mu$g protein/ml) at room temperature in the presence of the following: 10 mM Pipes/Tris buffer pH 7.0, 2 mM MgSO$_4$, 150 mM KCL, 9 $\mu$M valinomycin, 2 mM Na$_2$ATP, 0.1 mg/ml bovine serum albumin and 3 $\mu$M [$^{14}$C] aminopyrine (110 mCi/mmole). After 30 minutes the amount of AP accumulation was determined by rapid filtration.

Valinomycin was dissolved in methanol which was present in the assay at a concentration of 0.5%.

Compounds of structure (1) were dissolved in dimethylsulphoxide which up to the highest concentration used had no effect on AP accumulation.

(iii) Results

The compounds of the examples gave IC$_{50}$ values in the range of from 0.04 to 7.56 $\mu$M.

C. Rat: Lumen perfused stomach (pentagastrin stimulated gastric acid secretion)

Using a modification of the procedure described by Ghosh and Schild (Br. J. Pharmacology, 13, 54, 1958), the compounds of Examples 2 to 4, 7 to 10 were found on i.v. administration to cause an inhibition of pentagastrin stimulated gastric acid secretion of between 42 and 83% at 10 $\mu$mol/kg.

What we claim is:

1. A method of inhibiting gastric acid secretion which comprises administering to a mammal in need thereof an effective amount of a compound of structure (I):

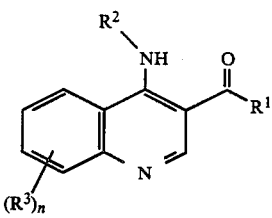

in which
- $R^1$ is hydrogen, $C_{1-6}$alkyl, $C_{1-6}$alkoxyl $C_{1-6}$alkyl, $C_{3-6}$cycloalkyl, $C_{3-6}$cycloalkyl $C_{1-6}$alkyl, phenyl, phenyl $C_{1-6}$alkyl, the phenyl groups being unsubstituted or substituted by 1 to 3 radicals selected from $C_{1-6}$alkyl, $C_{1-6}$alkoxy, amino, $C_{1-6}$alkylthio, or halogen;
- $R^2$ is $C_{1-6}$alkyl, $C_{3-6}$cycloalkyl, $C_{3-6}$cycloalkyl-$C_{1-6}$alkyl, phenyl, phenyl $C_{1-6}$alkyl or phenyl substituted by 1-3 radicals selected from $C_{1-6}$alkyl, $C_{1-6}$alkoxy, amino, $C_{1-6}$alkylthio, halogen, or hydroxy;
- $R^3$ is $C_{1-6}$alkyl, $C_{1-6}$alkoxy, $C_{1-6}$alkylthio, $C_{1-6}$alkanoyl, amino, $C_{1-6}$alkylamino, di-$C_{1-6}$alkylamino, or halogen; and
- n is 0, 1 or 2, provided that when n is 2 and $R^3$ has 4 to 6 carbon atoms, the $R^3$ groups are para or meta to each other;

or a pharmaceutically acceptable salt thereof.

2. A method of treatment of gastrointestinal diseases and other conditions caused or exacerbated by gastric acidity which comprises administering to a mammal in need thereof an effective amount of a compound according to claim 1.

3. A method to claim 1 in which the compound is 3-butyryl-4-(2-methylphenylamino)-8-methoxyquinoline.

4. A method according to claim 2 in which the compound is 3-butyryl-4-(2-methylphenylamino)-8-methoxyquinoline.